US009111655B2

(12) United States Patent
Ohashi et al.

(10) Patent No.: US 9,111,655 B2
(45) Date of Patent: Aug. 18, 2015

(54) RADIATION GENERATING APPARATUS AND RADIATION IMAGING SYSTEM

(71) Applicant: CANON KABUSHIKI KAISHA, Tokyo (JP)

(72) Inventors: Yasuo Ohashi, Hadano (JP); Yoichi Ikarashi, Fujisawa (JP); Yoichi Ando, Inagi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 107 days.

(21) Appl. No.: 13/927,755

(22) Filed: Jun. 26, 2013

(65) Prior Publication Data

US 2014/0023176 A1 Jan. 23, 2014

(30) Foreign Application Priority Data

Jul. 23, 2012 (JP) ................................. 2012-162245

(51) Int. Cl.
*G21K 1/04* (2006.01)
*A61B 6/06* (2006.01)
*A61B 6/08* (2006.01)

(52) U.S. Cl.
CPC ... *G21K 1/04* (2013.01); *A61B 6/06* (2013.01); *A61B 6/08* (2013.01)

(58) Field of Classification Search
CPC .............. A61B 6/00; A61B 6/08; A61B 6/06; A61B 6/587; A61B 6/4291; G21K 1/04; H05G 1/02; G03B 42/02; G01N 23/04
USPC .............. 378/62, 63, 145, 161, 205, 206, 147
See application file for complete search history.

(56) References Cited

U.S. PATENT DOCUMENTS

| | | | | |
|---|---|---|---|---|
| 3,600,570 A | * | 8/1971 | Okada ........................... | 362/330 |
| 3,919,559 A | * | 11/1975 | Stevens ......................... | 378/154 |
| 4,788,094 A | * | 11/1988 | Morita et al. ................. | 428/136 |
| 2004/0188645 A1 | * | 9/2004 | Arakawa ....................... | 250/583 |
| 2004/0228439 A1 | * | 11/2004 | Tsujii .............................. | 378/62 |
| 2006/0268409 A1 | * | 11/2006 | Tan et al. ...................... | 359/487 |
| 2008/0279330 A1 | * | 11/2008 | Ueki .............................. | 378/63 |

FOREIGN PATENT DOCUMENTS

| | | |
|---|---|---|
| JP | H07-148159 A | 6/1995 |
| JP | 2011-078578 A | 4/2011 |
| JP | 2011-104154 A | 6/2011 |

OTHER PUBLICATIONS

Jensen et al., Improvements in low power, end-window, transmission-target X-ray tubes, 2004, International Centre for Diffraction Data, Advances in X-ray Analysis, vol. 47, p. 64, 65, 69.*

* cited by examiner

*Primary Examiner* — Glen Kao
*Assistant Examiner* — Julio M Duarte-Carvajali
(74) *Attorney, Agent, or Firm* — Fitzpatrick, Cella, Harper & Scinto

(57) ABSTRACT

Provided is a radiation generating apparatus, including: a radiation generating unit for emitting radiation; and a movable diaphragm unit including a light projecting/sighting system for making a simulation display of a radiation field with visible light. The light projecting/sighting system includes: a light source of the visible light; a light guiding plate that is provided across a radiation axis, and causes the visible light from the light source to exit from a front surface of the light guiding plate; and a louver that gives directivity to the visible light exiting from the front surface of the light guiding plate.

16 Claims, 3 Drawing Sheets

RADIATION GENERATING APPARATUS AND RADIATION IMAGING SYSTEM

BACKGROUND OF THE INVENTION

1. Field of the Invention

The present invention relates to a radiation generating apparatus including a movable diaphragm unit including a light projecting and sighting system (hereinafter, referred to as "light projecting/sighting system") for making a simulation display of a radiation field as a visible light field, and to a radiation imaging system using the radiation generating apparatus.

2. Description of the Related Art

A typical radiation generating apparatus includes a radiation generating unit including a radiation tube and a movable diaphragm unit provided on a front surface of a radiation transmission window of the radiation generating unit.

As disclosed in Japanese Patent Application Laid-Open No. H07-148159, the movable diaphragm unit includes a light projecting/sighting system including a reflecting plate that transmits radiation and reflects visible light and a light source of visible light. The movable diaphragm unit further includes limiting leaves for defining a radiation field and a visible light field formed correspondingly thereto. The light source is provided off an irradiation path of radiation which irradiates a necessary radiation field so as not to interfere with the radiation when emitted. The reflecting plate is provided so as to be slanted with respect to a central axis of the radiation in order to reflect visible light from the light source provided in this way to form a visible light field for making a simulation display of the radiation field. Further, the light source and the reflecting plate are, together with the limiting leaves, provided in an envelope which blocks radiation. The envelope is formed of a material which can attenuate radiation that impinges on the reflecting plate and the limiting leaves to be dispersed.

However, in the conventional movable diaphragm unit, the reflecting plate of the light projecting/sighting system is provided so as to be slanted, and thus, the envelope covering the reflecting plate becomes large, which is a factor in hindering size reduction of the radiation generating apparatus and a radiation imaging system using the radiation generating apparatus. Further, the material for forming the envelope which can attenuate radiation is a heavy mass material, and thus, there is a problem of increased weight.

On the other hand, the conventional movable diaphragm unit has an advantage in that, when the radiation tube provided in the radiation generating apparatus is a reflection type radiation tube, the reflecting plate provided so as to be slanted can alleviate, by the heel effect, the radiation quantity and radiation quality distribution. However, when a radiation tube of a transmission type which does not cause the heel effect is used, the reflecting plate provided so as to be slanted generates the radiation quantity and radiation quality distribution.

SUMMARY OF THE INVENTION

It is an object of the present invention to reduce the size and the weight of a movable diaphragm unit including a light projecting/sighting system and to inhibit the radiation quantity and radiation quality distribution when a radiation tube of a transmission type is used.

In order to solve the above mentioned problem, according to an aspect of the present invention, there is provided a radiation generating apparatus, including; a radiation generating unit for emitting radiation; and a movable diaphragm unit including a light projecting/sighting system for making a simulation display of a radiation field with visible light, in which the light projecting/sighting system includes; a light source of the visible light, the light source being provided outside a path of the radiation that irradiates the radiation field, a light guiding plate provided across a radiation axis so as to cover the path of the radiation that irradiates the radiation field, the light guiding plate being configured to transmit the radiation and cause the visible light from the light source to exit from a front surface of the light guiding plate; and a louver configured to transmit the radiation and partition a region from which the visible light exits on the front surface of the light guiding plate.

Further features of the present invention will become apparent from the following description of exemplary embodiments with reference to the attached drawings.

DESCRIPTION OF THE EMBODIMENT

In the following, an exemplary embodiment of the present invention is described in detail with reference to the attached drawings. Throughout the figures referred to in the following, like reference symbols are used to designate like components.

Figure 1:
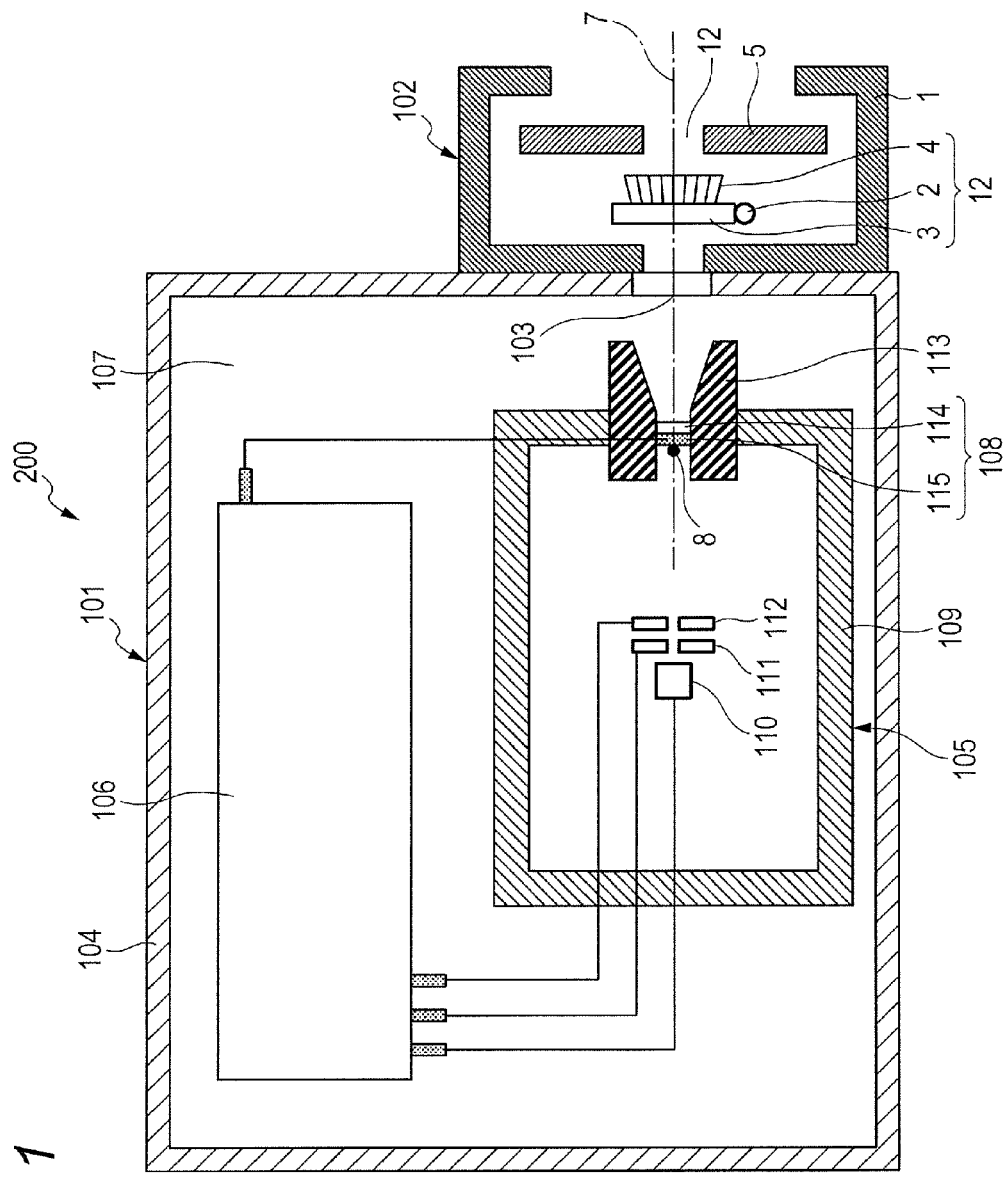
FIG. 1 is a schematic view illustrating a radiation generating apparatus according to an embodiment of the present invention.

FIG. 1 is a schematic view illustrating a structure of a radiation generating apparatus according to the present invention.

A radiation generating apparatus 200 includes a radiation generating unit 101 and a movable diaphragm unit 102.

The radiation generating unit 101 includes a housing 104 having a radiation transmission window 103, a radiation tube 105 that is housed in the housing 104 and is a supply source of radiation, and a drive circuit 106 for driving the radiation tube 105. The space remaining in the housing 104 is filled with an insulating liquid 107 that has the function of maintaining electrical insulation inside the housing 104 and serves as a cooling medium for the radiation tube 105.

It is desired that the housing 104 be strong enough as a container and be excellent in heat dissipation. Exemplary suitable materials used for forming the housing 104 include a metal material such as brass, iron, or stainless steel.

The radiation tube 105 is a transmission type radiation tube, and includes a vacuum container 109 having a target 108 mounted to a window portion thereof, and a cathode 110, a grid electrode 111, and a lens electrode 112 provided in the vacuum container 109. Further, a shielding member 113 is provided so as to surround the target 108, which blocks unnecessary radiation.

The target 108 is formed by providing a target layer 115 for generating radiation through electron irradiation on a support substrate 114 which satisfactorily transmits radiation, and is mounted under a state in which a side thereof which has the target layer 115 provided thereon is on the inner side. As the target layer 115, for example, tungsten, tantalum, or molybdenum is used. The target layer 115 is electrically connected to the drive circuit 106 and forms part of an anode.

The barrel of the vacuum container 109 is formed of an insulating tube of an insulating material such as glass or ceramic so as to maintain a vacuum of the inside thereof and to electrically insulate between the cathode 110 and the anode including the target layer 115. The pressure inside the vacuum container 109 is reduced for the purpose of causing the cathode 110 to function as an electron source. It is preferred that the vacuum thereof be about $10^{-4}$ Pa to $10^{-8}$ Pa.

The cathode 110 is an electron source and is provided so as to be opposed to the target layer 115 of the target 108. As the cathode 110, for example, a hot cathode such as a tungsten filament or an impregnated cathode, or a cold cathode such as a carbon nanotube can be used. The cathode 110, the grid electrode 111, and the lens electrode 112 are electrically connected to the drive circuit 106, and predetermined voltages are applied thereto. A voltage Va applied between the cathode 110 and target layer 115 depends on the use of the radiation, but generally is about 10 kV to 150 kV.

Electrons that are derived from the cathode 110 are converged by the lens electrode 112 and enter the target layer 115 of the target 108, to thereby generate radiation. The generated radiation passes through the support substrate 114 of the target 108, and further, through the radiation transmission window 103, the radiation is emitted to the outside of the radiation generating unit 101.

The movable diaphragm unit 102 is provided outside the radiation transmission window 103 provided in the housing 104 of the radiation generating unit 101. The movable diaphragm unit 102 includes an envelope 1 that surrounds the radiation transmission window 103, and a light projecting/sighting system 12 and limiting leaves 5 that are provided in the envelope 1. The light projecting/sighting system 12 includes a light source 2 of visible light, a light guiding plate 3, and a louver 4.

The envelope 1 has the effect of blocking radiation and, for example, blocks radiation reflected by the light guiding plate 3 and the limiting leaves 5, to thereby prevent surplus exposure to radiation. The envelope 1 is formed of a material which has the effect of blocking radiation, and a metal such as lead, tungsten, or tantalum, an alloy thereof, or the like may be used. Alternatively, by forming the envelope 1 using a metal such as aluminum or a synthetic resin which is less effective in blocking radiation, and providing thereto a metal sheet which has the enhanced effect of blocking radiation, the weight can be reduced.

Figure 2A:
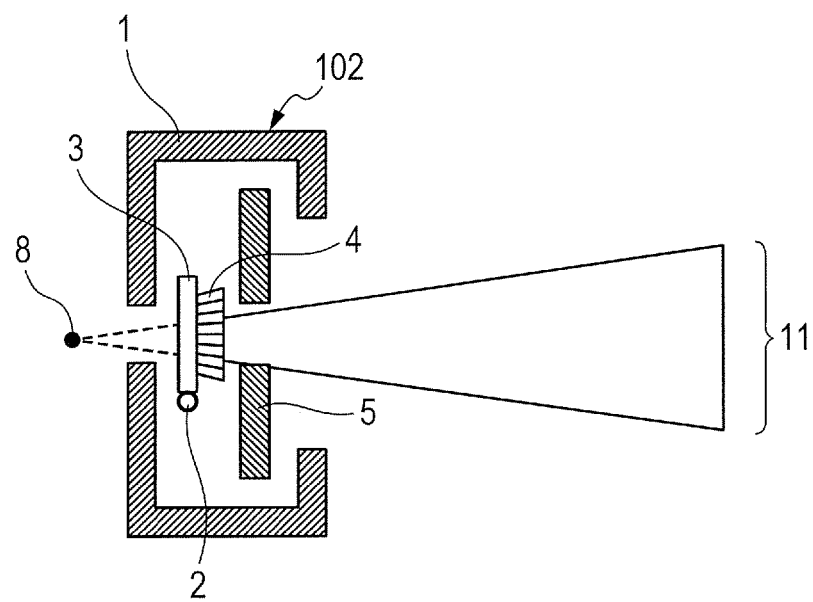
FIGS. 2A and 2B are schematic views of a movable diaphragm unit according to the present invention.
Figure 2B:
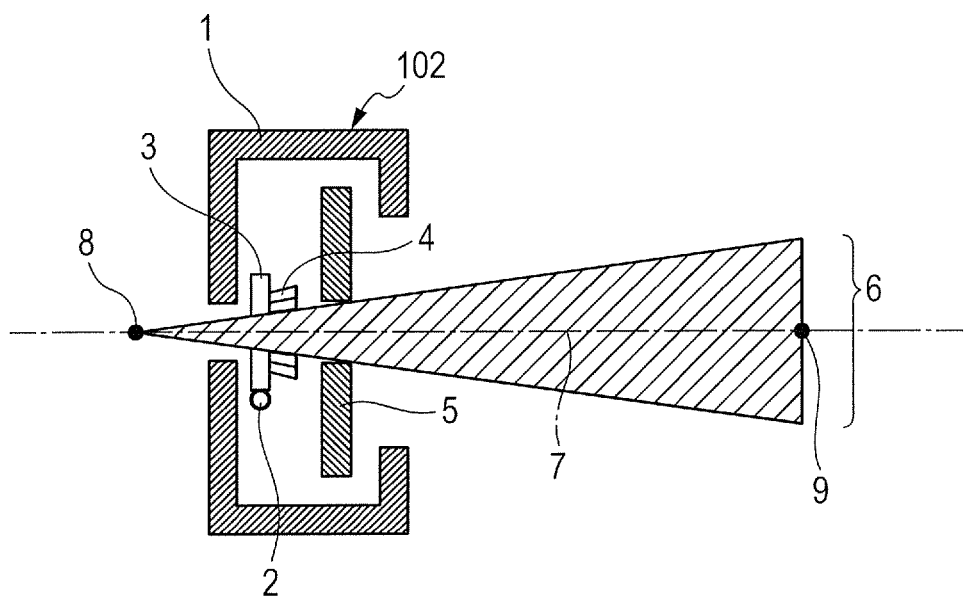

FIGS. 2A and 2B are schematic views of the movable diaphragm unit according to the present invention. FIG. 2A illustrates the movable diaphragm unit when visible light is emitted, and FIG. 2B illustrates the movable diaphragm unit when radiation is emitted. The light source is provided outside the path of radiation which irradiates a radiation field 6 (a diagonally shaded portion in FIG. 2B). It is enough that the light source 2 emits visible light and irradiates a range corresponding to the radiation field 6 with visible light of satisfactory brightness, and as the light source 2, for example, an incandescent lamp, a halogen lamp, a xenon lamp, or a light-emitting diode (LED) can be used. Among those, an LED is preferred because of the easiness of size reduction thereof.

The light guiding plate 3 causes visible light that enters from the light source 2 to exit from a front surface thereof. The rear surface of the light guiding plate 3 is a ground glass-like surface having minute irregularities, and the light guiding plate 3 can be formed of a transparent synthetic resin plate having a reflecting material provided on the rear surface and three side surfaces thereof. An LED as the light source 2 is located so as to be opposed to the remaining one side surface on which the reflecting material is not provided. By causing visible light to enter from the one side surface on which the reflecting material is not provided, surface emission from the front surface can be performed. The light guiding plate 3 is formed of a light element material having high radiation transmittance, and as the light guiding plate 3, for example, a synthetic resin such as an acrylic resin can be used.

The light guiding plate 3 is provided in the envelope 1 so as to cross the path of radiation which irradiates the radiation field 6. The light guiding plate 3 is provided across a radiation axis 7 so as to cover the path of the radiation. The visible light exiting surface of the light guiding plate 3 can be in a direction orthogonal to a radiation axis 7, in order to reduce the whole volume of the movable diaphragm unit 102. The radiation axis 7 as used herein is a straight line that connects a radiation focus 8 and a center 9 of the radiation field 6 when the limiting leaves 5 are opened at the maximum. The radiation focus 8 as used herein is the center of a location at which radiation is generated, and is the center of an electron beam irradiation region of the target layer 115. The center 9 of the radiation field 6 as used herein is a location corresponding to, when a plate material having the same shape and size as those of the radiation field 6 and having a uniform thickness is assumed, the center of the gravity of the plate material.

Figure 3A:
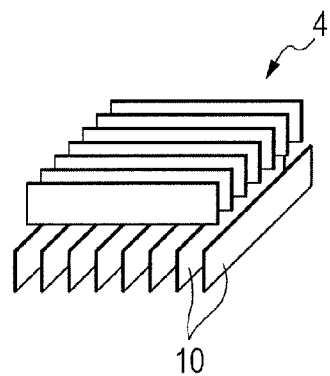
FIGS. 3A, 3B and 3C are schematic views of louvers according to the present invention.
Figure 3B:
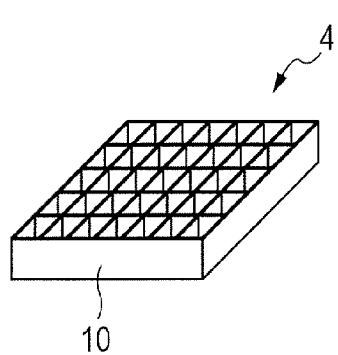
Figure 3C:
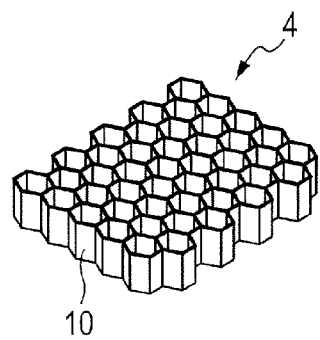

FIGS. 3A to 3C are perspective views of louvers according to the present invention. The louver 4 is provided on the front surface of the light guiding plate 3, for giving directionality to visible light exiting from the front surface of the light guiding plate 3. The louver 4 is an aggregation of partition walls 10, and partitions the region from which visible light exits and controls the direction of exiting light. The louver 4 illustrated in FIG. 3A has the shape of intersecting slits in two stages in which the multiple parallel plate-like partition walls 10 are arranged in directions perpendicularly intersecting each other, respectively. The louver 4 gives directionality to visible light exiting from the front surface of the light guiding plate 3 by partitioning, with the partition walls 102 in the two stages, the region from which the visible light exits into cells in a grid, and controlling the directions of visible light exiting from the respective cells in the grid. The louver 4 illustrated in FIG. 3B has the shape of a grid formed by crossing multiple plate-like partition walls 10 perpendicularly in one plane. The louver has the shape of a grid formed by the partition walls 10 in one stage, and gives directionality to visible light exiting from the front surface of the light guiding plate 3 by partitioning the region from which the visible light exits into cells in the grid, and controlling the directions of visible light exiting from the respective cells in the grid. The louver 4 illustrated in FIG. 3C has the shape of a honeycomb that is an aggregation of multiple hexagonal partition walls. The louver 4 gives directionality to visible light by causing the visible light to exit from the respective hexagonal regions and controlling the directions thereof. The louvers 4 illustrated in FIG. 3B and FIG. 3C have an advantage over the louver 4 illustrated in FIG. 3A in the easiness of size reduction thereof.

The louver 4 (partition walls 10) is formed of a light-blocking material that can transmit radiation and control the direction of exiting visible light. It is preferred that the louver 4 be formed of a light element having high radiation transmittance which blocks light. The louver 4 can be formed of, for example, a graphite foil, or paper or a synthetic resin film colored with a black coating such as carbon black so as to block light.

It is preferred that the aspect ratio, that is, the ratio between a width (or diameter) w and a height h (h/w) of a light exiting cell in the above-mentioned louver 4 in the shape of intersecting slits, in the shape of a grid, or in the shape of a honeycomb be 50 or more in order to give satisfactory directionality.

Further, it is preferred that the aspect ratio be 500 or less from the viewpoint of reducing space necessary for installing the apparatus.

It is preferred that the partition walls 10 of the louver 4 be slanted on the outer peripheral side under a state in which the amount of the slant is gradually increased from the radiation axis 7 side to the outer peripheral side. The slant allows directionality to be given to visible light so that the visible light expands similarly to the path of gradually expanding radiation for irradiation. It is preferred that the partition walls 10 be slanted so that extensions of the slanted surfaces of the partition walls 10 to the radiation generating unit 101 side converge to the radiation focus 8. The slant enables light from an imaginary light source located at the radiation focus 8 to form a visible light field 11 as illustrated in FIG. 2A, and the visible light field 11 having a size and a shape substantially the same as those of the radiation field 6 illustrated in FIG. 2B can be formed.

The limiting leaves 5 are formed of a material that blocks radiation and, as illustrated in FIG. 1, have an opening 12 for allowing passage of radiation formed at the center thereof. Radiation emitted from the radiation generating unit 101 passes through the opening 12 to be emitted to the outside, to thereby form the radiation field 6. By adjusting the size of the opening 12, the size of the radiation field 6 can be adjusted.

As the limiting leaves 5, for example, two plate materials each having a notch or a hole, which are overlapped so that the notches or the holes are coincident with each other and so as to be slidingly movable with respect to each other, can be used. In this case, the opening 12 is formed as a portion at which the notches or the holes are coincident with each other. By sliding the two plate materials with respect to each other, the size of the opening 12 can be adjusted. Further, there can be used multiple plate materials overlapping with one another so as to be slidingly movable in a manner that the locations thereof are shifted from one another so as to form the opening 12 by surrounding the opening with the plate materials, or a structure like a shutter of a camera.

In using the radiation generating apparatus 200, ordinarily, prior to emission of radiation, the radiation field 6 is recognized by the naked eye through a simulation display of the visible light field 11. Visible light which enters the light guiding plate 3 from the light source 2 exits from the front surface of the light guiding plate 3, is given directionality by the louver 4, and passes through the opening 12 in the limiting leaves 5 to form the visible light field 11. In this state, the size of the opening 12 in the limiting leaves 5 is adjusted to be suitable for the size of the appropriate radiation field 6. After the size of the radiation field 6 is determined, the light source 2 is turned off, and the radiation generating unit 101 is driven.

Radiation generated from the radiation tube 105 passes through the radiation transmission window 103 to be emitted to the movable diaphragm unit 102. The radiation emitted to the movable diaphragm unit 102 passes through the light guiding plate 3, and part thereof further passes through the louver 4 and through the opening 12 in the limiting leaves 5, to thereby irradiate the predetermined radiation field 6 (see FIG. 2B).

The radiation tube 105 used in this embodiment is a transmission type radiation tube, but, according to the present invention, a radiation tube of a reflection type can also be used. However, the light projecting/sighting system 12 according to the present invention does not use a conventional reflecting plate provided so as to be slanted, and thus, the cancelling action of the heel effect in a radiation tube of a reflection type is less liable to be obtained.

By slidingly moving at least the light guiding plate 3 and the louver 4 when radiation is emitted, the light guiding plate 3 and the louver 4 can be retracted outside the path of radiation which irradiates the radiation field 6. Further, the entire light projecting/sighting system (the light source 2, the light guiding plate 3, and the louver 4) may be moved. When such a retracting mechanism is provided, the light guiding plate 3 and the louver 4 can be formed of a material which blocks radiation.

Figure 4:
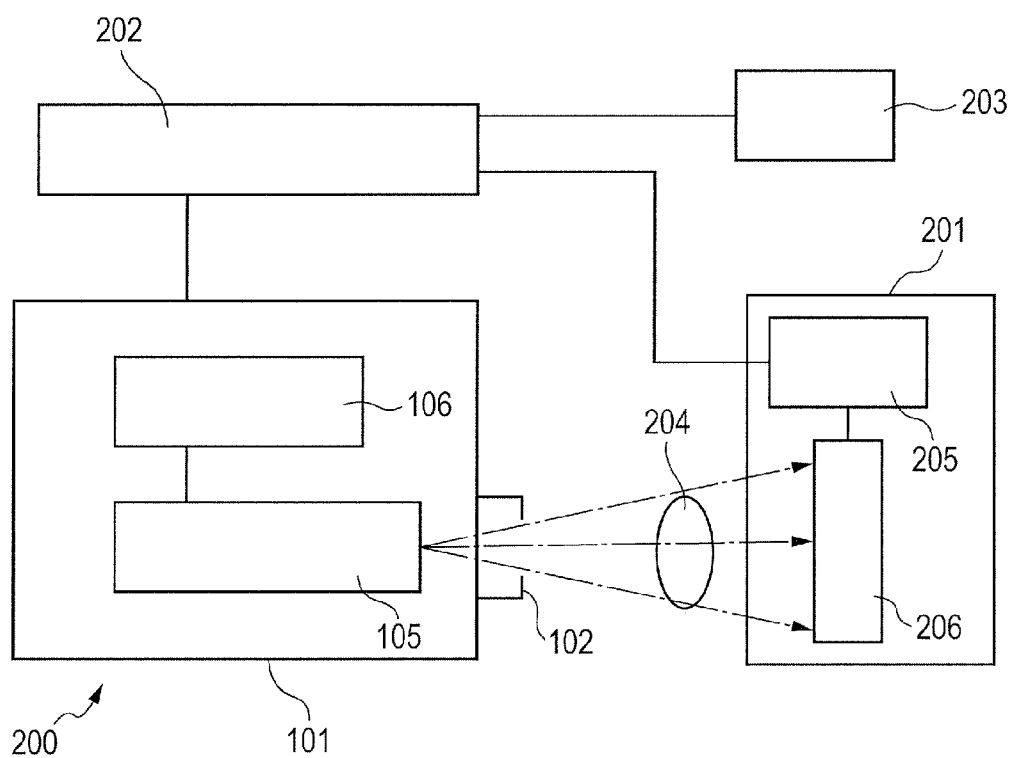
FIG. 4 is a block diagram illustrating a radiation imaging system according to an embodiment of the present invention.

Next, a radiation imaging system according to an embodiment of the present invention is described with reference to FIG. 4.

A system controlling apparatus 202 controls the radiation generating apparatus 200 and a radiation detecting apparatus 201 in a coordinated manner. The drive circuit 106 outputs various kinds of control signals to the radiation tube 105 under the control of the system controlling apparatus 202. Such a control signal controls the emission state of radiation emitted from the radiation generating apparatus 200. Radiation emitted from the radiation generating apparatus 200 passes through an subject 204 and is detected by a detector 206. The detector 206 converts detected radiation into an image signal and outputs the image signal to a signal processor 205. The signal processor 205 performs predetermined signal processing of the image signal under the control of the system controlling apparatus 202, and outputs the processed image signal to the system controlling apparatus 202. Based on the processed image signal, the system controlling apparatus 202 outputs, to a display apparatus 203, a display signal for causing the display apparatus 203 to display an image. The display apparatus 203 displays, on a screen, an image based on the display signal as an image of the subject 204. A representative example of the radiation is X-rays. The radiation generating apparatus and the radiation imaging system according to the present invention can be used as an X-ray generating apparatus and an X-ray image taking system, respectively. The X-ray image taking system can be used for non-destructive testing of an industrial product or pathological diagnosis of a human or an animal.

Example

A radiation imaging system using the radiation generating apparatus 200 as illustrated in FIG. 1 was manufactured.

The manufactured envelope 1 of the movable diaphragm unit 102 was sized to be 50×50×30 mm. A resin sheet containing tungsten powder was attached to inner surfaces of the envelope 1 for preventing leakage of diffused radiation. The light source 2 which was an LED, the light guiding plate 3, and the louver 4 were provided in the envelope 1. The louver 4 was provided adjacent to the front surface of the light guiding plate 3 so that directionality was able to be given by the louver 4 to visible light from the light source 2 which exited from the front surface of the light guiding plate 3. As the light guiding plate 3, an acrylic resin plate was used. In the acrylic resin plate, the rear surface had ground glass-like irregularities formed thereon, the rear surface and three side surfaces except a side surface opposed to the light source 2 had a reflecting material provided thereon, and surface emission was possible from the front surface by light emission from the light source 2. The louver 4 had the shape of the intersecting slits illustrated in FIG. 3A, and was an aggregation of the partition walls 10 formed of a plate-like (tape-like) graphite foil having a thickness of about 75 µm and a width of 2.5 mm. The partition walls were provided in two stages in which the parallel partition walls 10 at intervals of about 50 µm were arranged in directions perpendicularly intersecting each other, respectively, under a state in which the angle of the partition walls 10 was changed so that extensions of exiting visible light to the radiation generating unit 101 side converged to the radiation focus 8. Further, the limiting leaves 5 were provided in the envelope 1 so that the size of the radiation field 6 was able to be adjusted.

The above-mentioned movable diaphragm unit 102 was mounted to the radiation generating unit 101 to manufacture the radiation generating apparatus 200 illustrated in FIG. 1. Operation of a radiation imaging system using the radiation generating apparatus 200 was confirmed. As a result, it was confirmed that it was possible to form the visible light field 11 substantially coincident with the radiation field 6. When radiation was emitted, it was possible to obtain a satisfactory image without a shadow of the louver 4 and without the heel effect. Further, the weight of the entire movable diaphragm unit 102 was measured to be about 200 g, which meant that it was possible to attain significant weight reduction compared with a conventional unit.

Comparative Example

A conventional ordinary movable diaphragm unit was manufactured using a light source, which was a tube lamp having a diameter of about 20 mm, and a reflecting plate provided so as to be slanted with respect to the radiation axis. The envelope was sized to be 200×200×150 mm, and weighed about 2 kg.

The radiation generating apparatus according to the present invention can form the visible light field without using a reflecting plate, by emitting visible light emitted from the light source through the light guiding plate and the louver. The light guiding plate is provided perpendicularly to the radiation axis. Thus, large space necessary for installing, for example, a reflecting plate provided so as to be slanted with respect to the radiation axis is not necessary, and the envelope which houses the light guiding plate can be downsized accordingly. Therefore, the size and the weight of the envelope can be reduced, and, by extension, the sizes and the weights of the radiation generating apparatus and the radiation imaging system can be reduced. Further, the amount of radiation absorbed by the light guiding plate is smaller than that absorbed by a metal which is ordinarily used for a reflecting plate, and thus, radiation quality distribution generated when a radiation tube of a transmission type is used can be inhibited. The radiation imaging system using the radiation generating apparatus according to the present invention can take a satisfactory image using radiation of uniform radiation quality.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-162245, filed Jul. 23, 2012, which is hereby incorporated by reference herein in its entirety.

What is claimed is:

1. An X-ray generating apparatus, comprising:
    an X-ray generating unit having a target and an electron source emitting an electron beam toward said target so as to form a focal spot on said target; and
    a light projecting and sighting unit that comprises:
        a movable diaphragm unit having a plurality of limiting leaves;
        a light source emitting visible light;
        a light guiding plate provided across an X-ray axis so as to cover the path of the X-ray that irradiates an X-ray field, the light guiding plate being configured to transmit the X-ray and cause the visible light from said light source to exit from a front surface of said light guiding plate; and
        an X-ray transmissive louver having a plurality of partition walls defining an opening between two adjacent partition walls of the plurality of partition walls so as to transmit the X-ray and give directionality to the visible light emitted from said front surface,
    wherein said X-ray transmissive louver is secured at said front surface of said light guiding plate and is located between said light guiding plate and said limiting leaves so as to indicate a simulated X-ray irradiation field with visible light on a subject.

2. The X-ray generating apparatus according to claim 1, wherein said X-ray transmissive louver comprises any one of a graphite foil, paper that blocks light, and a synthetic resin film that blocks light.

3. The X-ray generating apparatus according to claim 1, wherein said X-ray transmissive louver comprises light exiting cells formed of intersecting slits that are formed by arranging, in two stages, multiple plate-like partition walls in directions intersecting each other, respectively.

4. The X-ray generating apparatus according to claim 3, wherein said light exiting cells each have an aspect ratio that is a ratio h/w between a width w and a height h of 50 or more and 500 or less.

5. The X-ray generating apparatus according to claim 3, wherein said multiple plate-like partition walls are slanted on an outer peripheral side in a state in which an amount of the slant is gradually increased from the X-ray axis side to the outer peripheral side.

6. The X-ray generating apparatus according to claim 5, wherein slanted surfaces of said multiple plate-like partition walls comprise slanted surfaces that, when said slanted surfaces are extended to the X-ray generating unit side, converge to an X-ray focus.

7. The X-ray generating apparatus according to claim 1, wherein said X-ray transmissive louver comprises light exiting cells formed into a grid by crossing and combining multiple plate-like partition walls in one plane.

8. The X-ray generating apparatus according to claim 1, wherein said X-ray transmissive louver comprises light exiting cells formed into a shape of a honeycomb that is an aggregation of multiple hexagonal partition walls.

9. The X-ray generating apparatus according to claim 1, wherein said light guiding plate and said X-ray transmissive louver are configured to be retracted outside the path of the X-ray that irradiates the X ray field.

10. The X-ray generating apparatus according to claim 1, wherein said X-ray generating unit comprises a transmitting type X-ray tube.

11. The X-ray generating apparatus according to claim 10, wherein said transmitting type X-ray tube has a transmitting type target having a target layer and a transmitting member supporting said target layer, and wherein the front surface of said light guiding plate is parallel to said target layer.

12. The X-ray generating apparatus according to claim 1, wherein said light guiding plate is disposed in a direction orthogonal to the X-ray axis.

13. An X-ray imaging system, comprising:
    the X-ray generating apparatus according to claim 1;
    an X-ray detecting apparatus for detecting the X-ray that is emitted from said X-ray generating apparatus and passes through a subject; and a controlling apparatus for controlling said X-ray generating apparatus and the said X-ray detecting apparatus in a coordinated manner.

14. The X-ray generating apparatus according to claim 1, wherein said light source is located outside an imaginary conic X-ray beam passing through an opening defined with said limiting leaves.

15. The X-ray generating apparatus according to claim 1, wherein the front surface of said light guiding plate is located in opposition to an opposite surface facing said focal spot.

16. The X-ray generating apparatus according to claim 1, wherein said X-ray transmissive louver has a varied pitch of the plurality of partition walls along an X-ray irradiation axis, and wherein a pitch at a limiting leaves side is wider than that at a light guiding plate side.

* * * * *